United States Patent [19]

Wiseman et al.

[11] Patent Number: 4,580,899
[45] Date of Patent: Apr. 8, 1986

[54] FLAMELESS SPECTROSCOPY

[75] Inventors: Alan G. Wiseman, Glen Waverley; Martin K. Masters, Pakenham Upper, both of Australia

[73] Assignee: Varian Associates, Inc., Palo Alto, Calif.

[21] Appl. No.: 402,519

[22] Filed: Jul. 28, 1982

[30] Foreign Application Priority Data

Jul. 28, 1981 [AU] Australia .............................. PE9946

[51] Int. Cl.⁴ .............................................. G01J 21/74
[52] U.S. Cl. .................................................... 356/312
[58] Field of Search ......................................... 356/312

[56] References Cited

U.S. PATENT DOCUMENTS 4,022,530  5/1977  Braun et al. .......................... 356/312
4,098,554  7/1978  Huber et al. .......................... 356/312

FOREIGN PATENT DOCUMENTS 6143  1/1981  Japan .................................... 356/312

OTHER PUBLICATIONS

Perkin-Elmer Catalog—Atomic Absorption HGA-500 Graphite Furnace—Aug. 1978.

Primary Examiner—F. L. Evans
Attorney, Agent, or Firm—Stanley Z. Cole; Edward H. Berkowitz

[57] ABSTRACT

A method and apparatus for mounting the tubular furnace of spectroscopic apparatus to enable a protective atmosphere. The furnace is supported within the housing by annular electrodes engaging opposite ends of the furnace and an annular chamber surrounds the furnace for substantially its full length. A gas feed chamber adjacent each end of the furnace communicates with the respective adjacent end of the furnace through the central opening of the adjacent electrode and also communicates with the adjacent end of the annular chamber through passages provided in the adjacent electrode. Gas is fed simultaneously from each feed chamber into each end of the furnace and annular chamber to flow axially therealong for discharge through an opening in a wall of the housing located intermediate the furnace ends. According to another aspect, one of the electrodes forms part of a movable door which is operative to open and close one end of the housing chamber containing the furnace, and resilient means acts between that electrode and another part of the door assembly to resiliently urge the electrode against the furnace in the closed condition of the door. According to yet another aspect, the furnace has part-spherical end surfaces for engaging the electrodes and is counterbored at each end to form a raised sample deposition zone.

8 Claims, 9 Drawing Figures

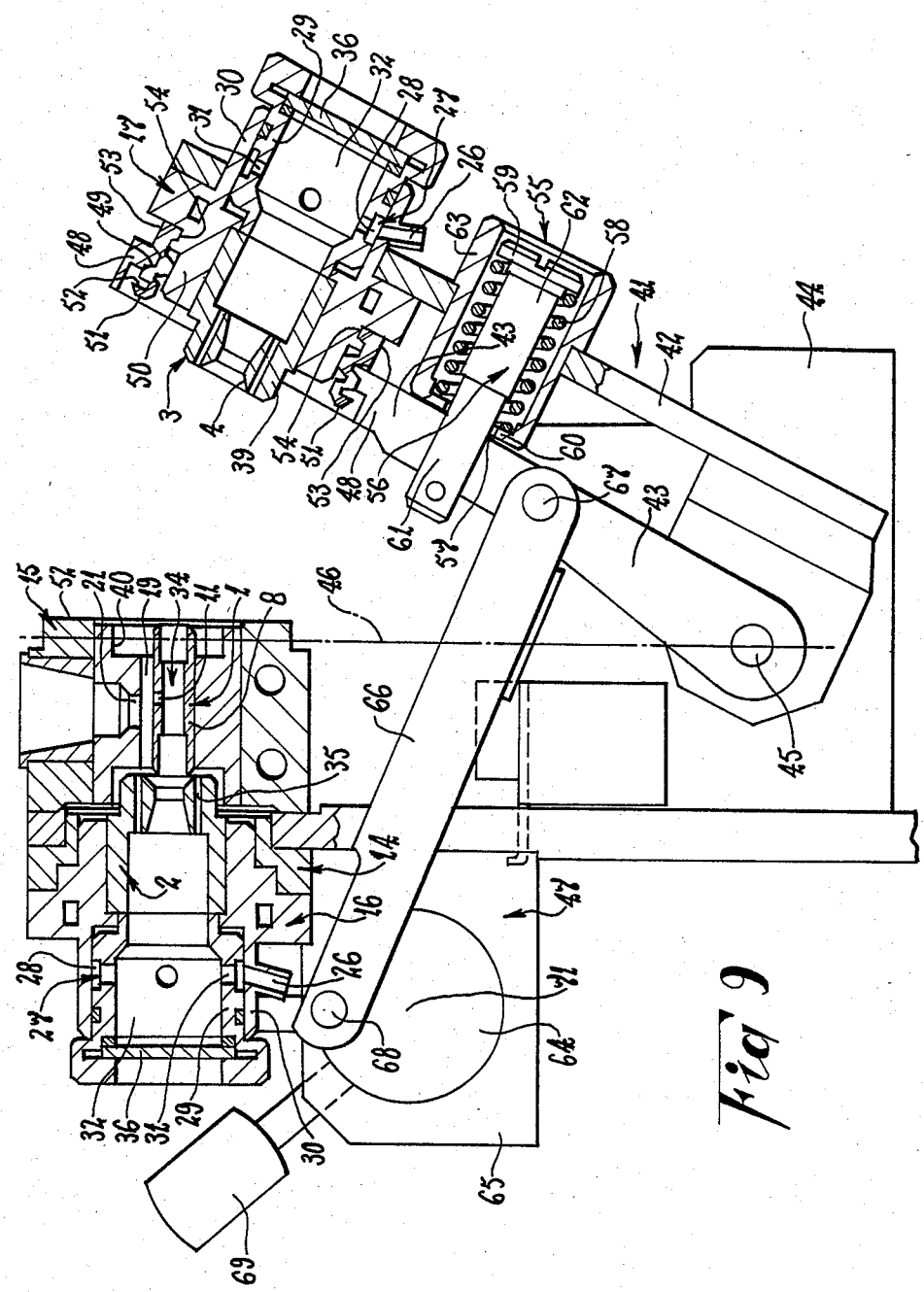

FLAMELESS SPECTROSCOPY

This invention relates to flameless spectroscopy and is particularly concerned with the nature of the furnace, its manner of mounting and the method of use. It will be convenient to hereinafter describe the invention with particular reference to a graphite tube furnace of the general type used in atomic absorption spectroscopy, but the invention in each of its aspects has wider applications.

Tubular furnaces as available prior to the present invention have suffered a variety of problems including inefficiency and/or unpredictability in heating, effectiveness of scavenging and shielding from oxidation, and accessability for replacement. The first two problems have a direct effect on the accuracy of analysis using such furnaces and the latter problem is inconvenient to the user of apparatus including such furnaces.

It is an object of the invention according to one of its aspects to provide an improved form of furnace of the graphite tube type. It is a further object of the invention according to another aspect to provide an improved method of providing a protective atmosphere for such furnaces. Still a further object of the invention according to yet another aspect is to provide an improved manner of mounting such a furnace whereby accessability is made relatively convenient. Yet another object of the invention is to provide furnace mounting means whereby the contact pressure on the furnace tube ends is maintained substantially constant.

According to one aspect of the present invention, there is provided a method of providing a protective atmosphere for a tubular furnace of spectroscopic apparatus, said method comprising locating said furnace within a housing so that a chamber surrounds said furnace for substantially the full length thereof, feeding gas into the interior of said furnace by simultaneously directing a respective stream of said gas into each end of said furnace to pass axially therealong, passing said gas from said furnace interior to said chamber through an opening in the wall of said furnace, feeding gas into said chamber by simultaneously directing a respective stream of said gas into each end of said chamber to pass axially therealong, and exhausting gas from said chamber through an outlet provided in said housing.

According to a further aspect of the invention, there is provided a furnace assembly for spectroscopic apparatus including a housing, a tubular furnace located within said housing and having an opening through the wall thereof, supporting means engaging each end of said furnace to support it within said housing, a gas flow chamber formed within said housing and surrounding said furnace for substantially the full length thereof, an outlet through a wall of said housing communicating with said gas flow chamber, two gas feed chambers formed within said housing adjacent respective said furnace ends, first passage means connecting each said feed chamber to the interior of said furnace through the adjacent said furnace end, and second passage means connecting each said feed chamber to a respective adjacent end of said flow chamber.

According to yet another aspect of the invention, there is provided a mounting assembly for a tubular furnace of spectroscopic apparatus, including a housing part, a chamber within said housing part for receiving a said furnace, a first electrode within said housing part at one end of said chamber for engagement with one end of a said furnace received within said chamber, an opening at the end of said chamber opposite said one end thereof through which said electrode can be introduced into and removed from said chamber, carrier means mounted for movement relative to said housing part, door means connected to said carrier means for movement therewith between closed and opened positions at which it closes and opens respectively the said opening, a second electrode attached to said door means for engagement with an end of said furnace opposite said one end thereof in said closed position of the door means, and resilient means forming at least part of the connection between said carrier means and said door means and which is operative to permit said carrier means to move relative to said door means beyond the position at which said door means is in said closed position.

According to still another aspect of the invention, there is provided a tubular furnace for spectroscopic apparatus, said furnace having a cylindrical outer surface and an annular electrode engaging surface at each end, each said annular surface sloping radially inwardly from said outer surface in a direction away from the opposite said end of the furnace and having a convex curvature between the radial inner and outer extremities thereof.

According to another aspect of the invention, there is provided a cylindrical tubular furnace for spectroscopic apparatus having a cylindrical passage therethrough, a counterbore formed at each end portion of said passage to form a sample deposition zone of reduced diameter intermediate the ends of said furnace, and a sample deposition opening formed radially through the wall of said furnace intermediate the ends thereof.

According to still a further aspect of the invention, there is provided a furnace assembly for spectroscopic apparatus including a housing part, a chamber within said housing part, a tubular furnace continued within said chamber so that an annular space is provided around said furnace for substantially the full length thereof, a first electrode connected to said housing part and engaging one end of said furnace, a second electrode engaging the opposite end of said furnace, resilient means urging said second electrode into firm engagement with said furnace, and two gas feed chambers each of which communicates with the interior of said furnace and with respective opposite ends of said annular space by way of passages formed through a respective one of said electrodes.

The various aspects of the invention identified above are interrelated in that they each contribute to improvements in the furnace or its mounting for spectroscopic apparatus, but they are not inter-dependant. That is, no aspect discussed above is entirely reliant on the coexistence of any one or more of the other aspects. Each aspect possesses advantages in its own right.

The essential features of the invention, and further optional features, are described in detail in the following passages of the specification which refer to the accompanying drawings. The drawings however, are merely illustrative of how the invention might be put into effect, so that the specific form and arrangement of the features (whether they be essential or optional features) shown is not to be understood as limiting on the invention.

IN THE DRAWINGS

FIG. 9 is a view similar to FIG. 8 but showing the housing in the open condition;

Figure 1:
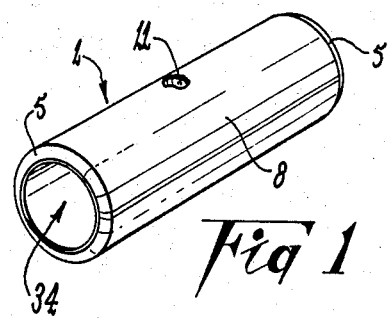
FIG. 1 is a perspective view of a typical furnace for spectroscopic apparatus to which one aspect of the invention can be applied.
Figure 2:
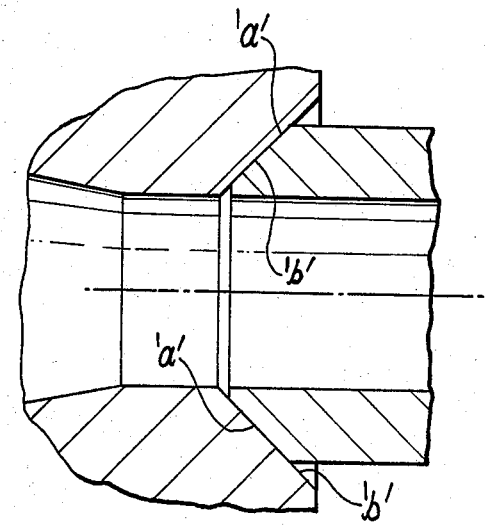
FIG. 2 is a cross sectional view of part of an electrode and engaging end portion of a furnace according to the prior art.

A typical furnace 1 to which one aspect of the invention can be applied, is shown in FIG. 1, and that furnace 1 may be composed of graphite or other suitable material. The furnace 1 is adapted to be mounted between two electrodes 2 and 3 (see FIG. 5), each of which has a frusto-conical internal end surface 4 (FIG. 3) against which a respective end of the furnace 1 engages. Under such circumstances in the past, it has been common practice to provide the furnace ends with flat faced chamfers having an angle of slope complementary to that of the furnace surface with which it engages, and such a prior art arrangement is shown in FIG. 2. In practice, it is found that with such prior arrangements full circumferential contact does not always occur between the furnace end 'a' and the electrode surface 'b' with the result that the heating characteristics of the furnace are disturbed.

Figure 4:
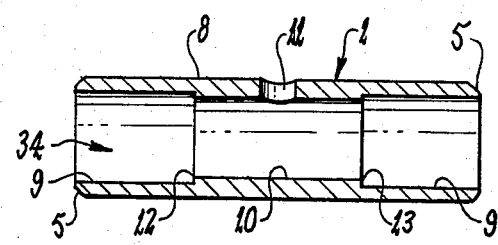
FIG. 4 is a longitudinal cross sectional view of the furnace shown in FIG. 1.
Figure 3:
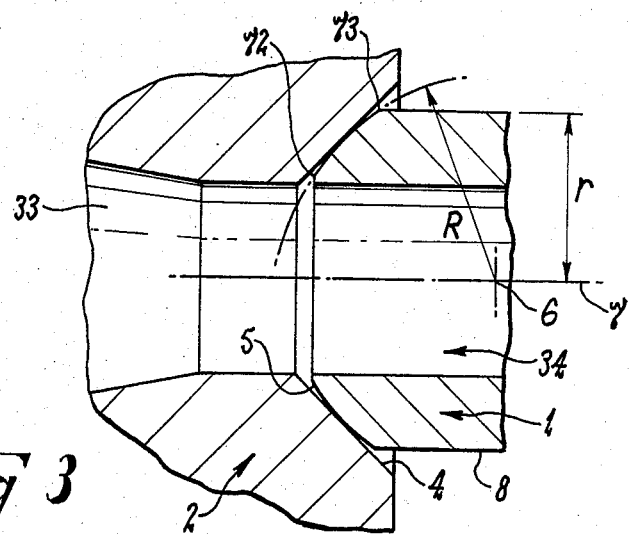
FIG. 3 is a view similar to FIG. 2 but showing the furnace end portion modified according to one aspect of the present invention.

That particular difficulty has been overcome in the furnace 1 as shown in FIGS. 1, 3 and 4 by adopting a curved chamfer face 5 at each end in place of the conventional flat chamfer face 'a' shown in FIG. 2. The curvature of each face 5 is convex between the radially inner and outer extremities 72 and 73 of that face as best seen in FIG. 3. Also as shown, the curvature of each surface 5 is preferably spherical having its centre 6 substantially coincident with the longitudinal axis 7 of the furnace 1. By way of example, the radius 'R' of the curved surface 5 may be 20 to 30% greater than the radius 'r' of the outer cylindrical surface 8 of the furnace 1. Such a surface configuration ensures full circumferential contact with the electrodes 2 and 3 thereby improving the heating characteristics and predictability of the furnace 1.

In the particular form shown in FIG. 4, the furnace 1 has a counterbore 9 formed in each end portion to create a central internal portion 10 of reduced diameter. A sample deposition opening 11 leads to that portion 10 so that the sample is deposited on a raised area formed by the portion 10 which, rather surprisingly, effectively retains the sample. That is, the sample has little tendency to spill over the boundaries 12 and 13 of the raised portion 10.

The reduced internal diameter at the axial centre of the furnace 1 has the further advantage of providing increased strength at a region which is susceptible to failure in prior furnaces. That dimensional characteristic also improves the temperature profile of the furnace 1 in that temperature variation over the length of the furnace 1 is minimised.

A furnace 1 having the dimensional characteristics just described may or may not have spherical end surfaces 5 as previously described. That is, the advantages inherent in those dimensional characteristics can be achieved without use of spherical end surfaces.

Figure 5:
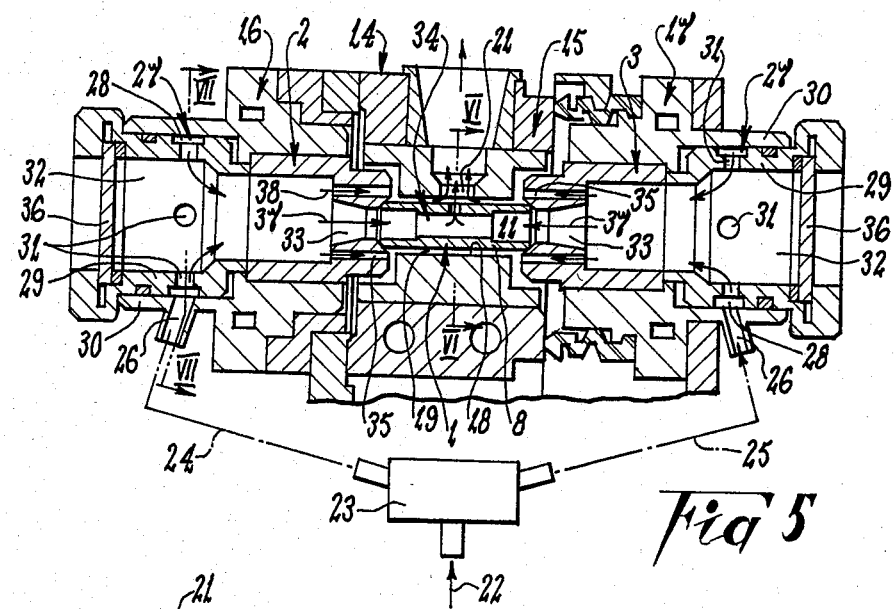
FIG. 5 is a cross sectional view of a furnace assembly according to one embodiment of the invention.

According to a further aspect of the invention, the tubular furnace 1, which may or may not be as particularly described above, is mounted in such a way as to enable use of an improved protective atmosphere system. The furnace is mounted between two annular electrodes 2 and 3 as shown in FIG. 5, each of which is carried by a furnace housing 14. As shown in FIG. 5, that housing 14 has an intermediate portion 15 arranged to fully surround the furnace 1 and two hollow end portions 16 and 17 associated with respective electrodes 2 and 3. The housing portions 15, 16 and 17 are preferably separable, but that is not essential for this particular aspect of the invention.

The intermediate housing portion 15 has a cylindrical chamber 18 within which the furnace 1 is received as shown in FIG. 5. The chamber, 18 surrounds the funnel in spaced relationship so that an annular space 19 exists between the outer cylindrical surface 8 of the furnace 1 and the adjacent internal surface 20 of the housing portion 15 (see FIG. 6). An outlet port 21 in the housing portion 15 communicates with the space 19 preferably at a location substantially mid-way in the axial length of the furnace 1. It is further preferred, as shown, that the saxple deposition opening 11 is aligned with the outlet port 21.

Figure 6:
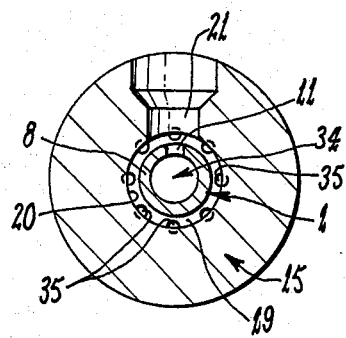
FIG. 6 is a cross sectional view taken along line VI—VI of FIG. 5.
Figure 7:
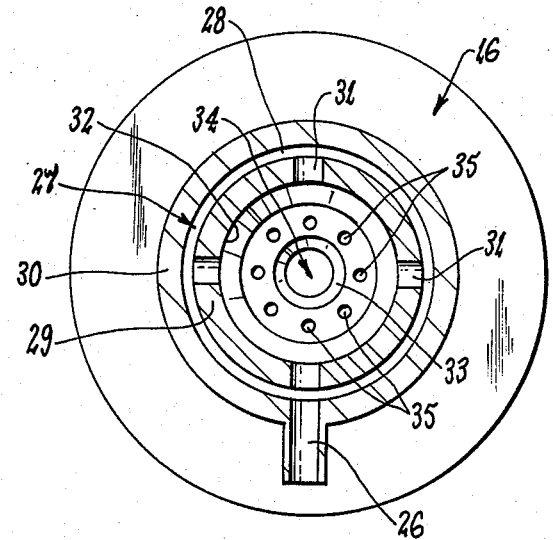
FIG. 7 is a cross sectional view taken along line VII—VII of FIG. 5.

A source of gas (not shown) is connected to each of the two housing end portions 16 and 17 and the gas will be selected according to particular requirements. Preferably, as shown, that gas source is connected through conduit 22 to a manifold or "T" junction 23 from which separate conduits 24 and 25 connect to a respective one of the housing end portions 16 and 17. In the particular construction shown, each of the end portions 16 and 17 includes an inlet port 26 which receives gas from the respective conduit 24 or 25 and a distribution manifold 27 which is in communication with the inlet port 26 and distributes the received gas around the interior of the housing end portion 16 or 17. As best seen in FIG. 6, the distribution manifold 27 may be defined by an annular space or groove 28 provided between inner and outer cylindrical sections 29 and 30 respectively of the housing end portion 16 or 17 and a plurality of circumferentially spaced openings 31 which connect the space 28 with the interior 32 of the inner section 29.

The interior 32 of each inner section 29 is preferably substantially coaxial with the adjacent annular electrode 2 or 3 as shown, and forms a gas feed chamber which communicates directly with the electrode bore 33 and consequently is also in direct communication with the furnace bore 34. A plurality of gas feed passages 35 are provided through each electrode 2 and 3 so as to provide communication between the adjacent gas chamber 32 and the annular space 19 surrounding the furnace 1. The passages 35 may be substantially evenly spaced in a circle coaxial with the respective electrode bore 33 and extend generally in the axial direction of the electrode 2 or 3. It will be appreciated that other means may be adopted to provide communication between each chamber 32 and the adjacent end of the annular space 19.

It is preferred that the end wall 36 of each gas feed chamber 32—i.e., the wall remote from the furnace 1—is formed by a transparent window so as to provide an unimpeded sight path through the furnace bore 34.

When the arrangement described is in use, gas enters each of the distribution manifolds 27 and is substantially evenly distributed around the interior of the related gas chamber 32 by way of the mainfold openings 31. The gas tends to flow axially through each chamber 32 towards the furnace 1 as shown and is split into two streams which are respectively represented by arrows 37 and 38 in FIG. 5. The stream 37 flows into the adjacent end of the furnace bore 34 through the central bore 33 of the associated electrode 2 or 3, and, the other stream 38 (which has several components) flows through the electrode passages 35 into the adjacent end of the annular space 19 surrounding the furnace 1. As the streams 37 and 38 enter the furnace 1 and annular space 19 from each of their respective ends, there is discharge of gas through the sample deposition opening 11 of the furnace 1 and thence through the outlet port 21 of the housing 14. The gas flow through the furnace 1 tends to scavenge the by-products of the sample drying and ashing stages and also helps to prevent oxidation, whereas the gas flow through the electrode passages 35 provides a protective atmosphere around the furnace 1.

If desired, the gas flow can be controlled as required to provide different flow rates at different times during the heating of the furnace 1. That control may be achieved through programmable means and solenoid valves or the like.

In the preferred construction shown, the furnace 1 is mounted in such a way as to facilitate replacement when necessary. That form of mounting may or may not be used with any one or more of the aspects previously described. It will be convenient however, to describe that mounting feature with reference to the previously described furnace housing arrangement.

The furnace mounting includes a separable housing which in the closed condition, encloses the furnace and supports it between a pair of electrodes. One part of the housing is preferably fixed while the other is movable between open and closed positions, although both parts may be movable if desired. The movable or door part of the housing is mounted on a carrier for movement between the open and closed positions and it is a feature of this aspect that the door is capable of limited movement relative to that carrier. It is a further feature that the door is resiliently biased on its carrier mounting for a purpose hereinafter made clear.

Figure 8:
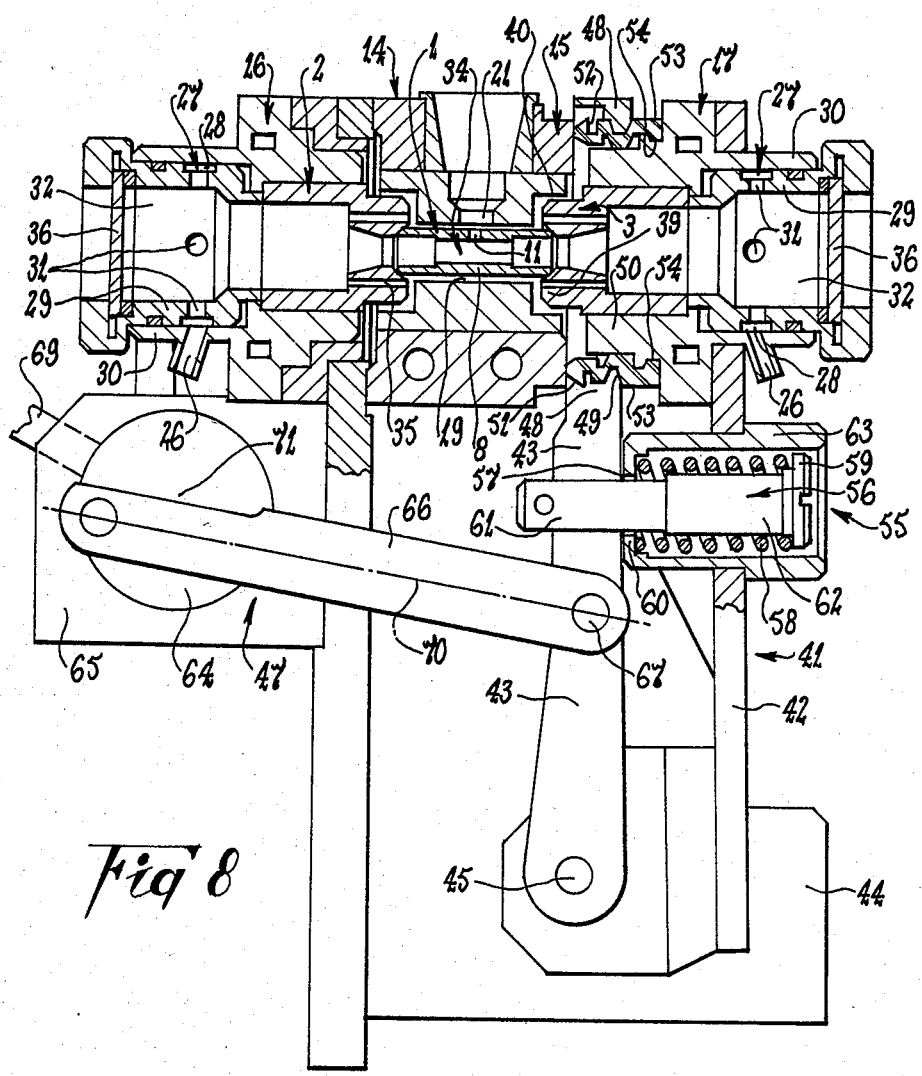
FIG. 8 is a view similar to FIG. 5 but showing associated mechanism for opening and closing the furnace housing.

In the preferred construction shown in FIGS. 8 and 9, the door part of the housing includes the end portion 17 previously described. That end portion 17 defines one of the gas feed chambers 32 and has the electrode 3 attached. According to the arrangement shown, the electrode 3 is partially contained within the outer cylindrical section 30 of the housing portion 17 and has a cylindrical front end portion 39 projecting axially beyond that outer section 30 as best seen in FIG. 9. That front end portion 39 contains the internal frusto-conical end face 4 for engagement with the adjacent end of the furnace 1, which is contained substantially within the housing intermediate portion 15 as previously described. With this arrangement it is preferred that the intermediate portion 15 has a counterbore 40 at the end to receive the front end portion 39 of the electrode 3 and, as shown, the furnace 1 extends into that counterbore 40 for engagement with the electrode 3.

The door carrier 41 may take any of several forms, but in the construction of FIGS. 8 and 9 includes a support member 42 and a control member 43 which are resiliently interconnected as hereinafter described. The support member 42 may be in the form of a plate or arm which carries the housing door portion 17 and is pivotally connected to a support 44 at a location 45 remote from that door portion 17. The axis of the pivotal connection 45 is transverse to the longitudinal axis of the furnace 1 and is preferably located in a plane 46 (FIG. 9) which is also transverse to that longitudinal axis and which passes through or lies close to the zone of engagement between the furnace 1 and the electrode 3. It is further preferred that the door portion 17 of the housing 14 extends both forwardly and rearwardly of its connection with the support member 42 as shown.

Actuating means 47 is connected to the support member 42 through the control member 43 which may also be in the form of a plate or arm and is preferably pivotally mounted in which event it is generally convenient to pivot it about the same axis as the support fiber 42, as shown. In the construction shown, the control member 43 is located between the support member 42 and the intermediate portion 15 of the housing 14 and has a collar section 48 which surrounds the junction between the housing portions 15 and 17 when the door portion 17 is the closed position as shown in FIG. 8. In that position, the furnace is supported between the electrodes 2 and 3 and the door portion 17 closes off the adjacent open end of the housing counterbore 40, at least to the extent that removal of the furnace 1 is prevented.

A resilient boot seal 49 may be connected between the collar section 48 and the adjacent cylindrical section 50 of the door portion 17 in order to provide a seal against escape of gas. An end part or ring 51 of the seal 49 is preferably arranged as shown to be pressed against an opposed surface 52 of the housing intermediate portion 15 when the housing door portion 17 is closed as shown in FIG. 8. The other end part 53 of the seal 49 is firmly located within a retainer groove 54 of the door portion 17 to provide a gas tight seal at that location.

According to the particular construction shown, a resilient interconnection 55 is provided between the support and control members 42 and 43 and is located between the housing 14 and the pivotal mounting 45 of the members 42 and 43. The particular resilient interconnection 55 shown includes a pin 56 attached to the control member 43 and extending laterally therefrom to pass freely through an aperture 57 in the support member 42. In the example construction shown, a helical spring 58 is arranged to coact between an enlarged head 59 of the pin 56 and a part 60 of the support member 42 so as to tend to draw the two members 42 and 43 towards one another (see FIG. 9). If desired, the pin 56 may be formed of two threadably connected parts—i.e., a stud 61 and a socket 62—which are adapted for relative rotation so as to vary the effective length of the pin 56 and thereby vary the spring pressure. As shown, the support mexber 42 includes a sleeve portion 63 which contains the spring 58 and forms the member part 60.

Any suitable actuating means 47 may be adopted for moving the carrier 41 between the door open and door closed positions as shown in FIGS. 9 and 8 respectively. In the form shown, the actuating means 47 includes a drive member 64 rotatably mounted on a support 65 for movement about an axis substantially parallel to the axis of the carrier pivot 45. The drive member 64 may be connected to the carrier 41 through a rigid link or bar 66 as shown. The link 66 is pivotally connected at one end to the control member 43 at a location 67 between the carrier pivot 45 and the housing 14, is pivotally connected at its, opposite end to the drive member 64 at a location 68 radially outwards of the rotational axis of the drive member 64. Rotation of the drive member 64 can be effected by way of a manually engagable handle 69 or by any other appropriate means.

The arrangement is such that rotation of the drive member 64 in one direction causes the door portion 17 to open (FIG. 9) and rotation in the opposite direction causes the door portion 17 to close (FIG. 8). The resilient interconnection 55 between the support and control members 42 and 43 of the carrier 41 enables the drive member 64 to be moved beyond the position at which the electrode 3 and furnace 1 engage (FIG. 8). That is, after the electrode 3 and furnace 1 engage further movement of the control member 43 in the door closing direction is resisted only by the spring 58. Thus, such further movement of the control member 43 can be effected and in so doing the connecting pin 56 is moved relative to the support member 42 so as to cause compression of the spring 58. In this way the furnace mounting means described enables repeatable and consistent pressure to be maintained between the furnace tube 1 and the electrodes 2 and 3. It is preferred that the drive member 64 can be rotated to an over-centre lock position as shown in FIG. 8. At that position, an imaginary line 70 (FIG. 8) joining the axes of the two end pivots 67 and 68 of the drive link 66 is slightly to one side of the rotational axis 71 of the drive member 64 and is moved to the other side of that axis 71 during the initial part of the door opening operation.

An arrangement as described is relatively simple yet effective. In particular, it has the advantage of ensuring a tight seal at the housing door without the need for extremely fine tolerances in manufacture and assembly of the relevant parts.

Finally, it is to be understood that various alterations, modifications and/or additions may be introduced into the constructions and arrangexents of parts previously described without departing from the spirit or ambit of the invention as defined by the appended claims.

Having now described our invention what we claim as new and desire to secure by Letters Patent is:

1. A method of providing a protective atmosphere for tubular furnace of spectroscopic apparatus, said method comprising locating said furnace within a housing so that a chamber surrounds said furnace for substantially the full length thereof, first dividing a primary gas flow symmetrically into two secondary gas flows and directing each said secondary gas flow toward the respective ends of said tubular furnace, further dividing each of said secondary gas flows into an interior gas flow and a plurality of substreams forming an exterior gas flow, feeding said interior gas flow into the interior of said furnace by simultaneously directing a respective stream of said gas into each end of said furnace to pass axially therealong, passing said interior gas flow from said furnace interior to said chamber through an opening in the wall of said furnace, feeding said exterior gas flow into said chamber by simultaneously directing said substreams in aximuthal symmetry about said tubular furnace to form a respective stream of said exterior gas flow into each end of said chamber to pass axially therealong, and exhausting gas from said chamber through an outlet provided in said housing.

2. A method according to claim 1, wherein said housing outlet and said furnace wall opening are in substantial alignment and are located substantially midway between said furnace ends.

3. A furance assembly for spectroscopic apparatus including a housing, a tubular furnace located within said housing and having an opening through the wall thereof, a pair of axially spaced annular electrodes arranged coaxial with said furnace and each engaging and supporting a respective end of said furnace, a portion of said housing extending between said electrodes and surrounding said furnace, a gas flow chamber formed between said housing portion and said furnace and surrounding said furnace for substantially the full length thereof, an outlet through a wall of said housing portion communicating with said gas flow chamber, two gas feed chambers formed within said housing adjacent respective said furnace ends, first passage means connecting each said feed chamber to the interior of said furnace through the adjacent said furnace end and comprising the central opening of a respective one of said electrodes, second passage means connecting each said feed chamber to a respective adjacent end of said flow chamber, and a common gas source connected to each said feed chambers.

4. A furnace assembly according to claim 3, wherein said flow chamber is annular and both said furnace opening and said housing outlet are located substantially midway between the ends of said furnace.

5. A furnace assembly to claim 4, wherein said furnace opening and said housing outlet are in substantial alignment.

6. A furnace assembly according to claim 5, wherein the central opening of each said annular electrode constitutes a respective one of said first passage means and each said second passage means comprises a plurality of passages formed through a respective one of said electrodes and extending generally axially thereof, said passages being arranged in a circle substantially concentric with said central opening.

7. A furnace assembly according to claim 3, wherein each said feed chamber is located in substantial axial alignment with the interior of said furnace and has one wall formed at least in part by a transparent window, whereby a beam of light can pass through each said gas feed chamber and axially through said furnace.

8. A furnace assembly according to claim 7, wherein a manifold surrounds each said feed chamber and is connectable to said common gas source, and each said manifold communicates with a respective one of said feed chambers at a plurality of locations around the axis of said furnace.

* * * * *

UNITED STATES PATENT AND TRADEMARK OFFICE
CERTIFICATE OF CORRECTION

PATENT NO. : 4,580,899

DATED : April 8, 1986

INVENTOR(S) : Alan G. Wiseman et al

It is certified that error appears in the above-identified patent and that said Letters Patent is hereby corrected as shown below:

On the title page assignee should read:

--(73) Assignee: Varian Techtron Pty, Limited ,
Mulgrave, Victoria, Australia --.

Signed and Sealed this

Eighth Day of July 1986

[SEAL]

Attest:

DONALD J. QUIGG

Attesting Officer

Commissioner of Patents and Trademarks